United States Patent [19]

Helmy

[11] Patent Number: 5,593,454
[45] Date of Patent: Jan. 14, 1997

[54] ARTIFICIAL LIMB MOUNTING APPARATUS

[76] Inventor: Nashat N. Helmy, 2035 Ordway Rd., Golden Valley, Minn. 55422

[21] Appl. No.: 371,742

[22] Filed: Jan. 12, 1995

[51] Int. Cl.$^6$ ........................................... A61F 2/78
[52] U.S. Cl. ................... 623/32; 623/33; 602/63; 2/22
[58] Field of Search .................. 623/32, 33, 34, 623/35, 36; 602/26, 62, 63; 2/16, 22, 59, 242

[56] References Cited

U.S. PATENT DOCUMENTS

| | | | |
|---|---|---|---|
| 3,322,873 | 5/1967 | Hitchcock | 2/167 |
| 3,600,717 | 8/1971 | McKeehan | 623/36 |
| 3,613,681 | 10/1971 | Adams | 602/63 |
| 4,084,586 | 4/1978 | Hettick | 128/157 |
| 4,479,272 | 10/1984 | Beldzisky | 623/32 |
| 4,635,626 | 1/1987 | Lerman | 623/36 |
| 4,822,371 | 4/1989 | Jolly et al. | 623/32 |
| 4,888,829 | 12/1989 | Kleinerman et al. | 2/167 |
| 4,908,037 | 3/1990 | Ross | 623/32 |
| 4,923,475 | 5/1990 | Gosthnian et al. | 623/37 |
| 5,168,577 | 12/1992 | Detty | 2/16 |
| 5,314,496 | 5/1994 | Harris et al. | 623/36 |
| 5,376,130 | 12/1994 | Courtney | 623/32 |
| 5,376,132 | 12/1994 | Caspers | 623/36 |
| 5,383,893 | 1/1995 | Daneshvar | 606/162 |

FOREIGN PATENT DOCUMENTS 1812982  4/1993  U.S.S.R. .................. 623/32

Primary Examiner—John G. Weiss
Assistant Examiner—Bruce E. Snow
Attorney, Agent, or Firm—Nawrocki, Rooney & Sivertson, P.A.

[57] ABSTRACT

An elastomeric sleeve, for retaining and attaching a prosthesis to a stump of an amputee. Typically, the sleeve is made of polyurethane, soft elastomer reinforced with a nylon or polyurethane mesh. This reinforcement, among other things, eliminates the possibility of support failure caused by a small tear or cut. The polyurethane elastomer is selected to have a resilience, load bearing capability and energy and impact absorption similar or close to that of the enclosed limb adjacent to the sleeve to reduce pressure points. The elastomer is also selected to be able to stretch up to 700% to 1,600% an original dimension but return to within five percent or less of the original dimension. These stretch characteristics are modified by a special mesh pattern, which permits a greater amount of stretch around the limb circumferentially than along the limb. This results in the limb remaining tightly secured to a prosthesis as the sleeve extends and compresses longitudinally in use, and also eases the task of stretching and installing the sleeve over the stump and prosthesis. This combination also provides a sealing grip around the stump while providing a soft and friendly attachment.

7 Claims, 3 Drawing Sheets

Fig. 1
Fig. 2
Fig. 3
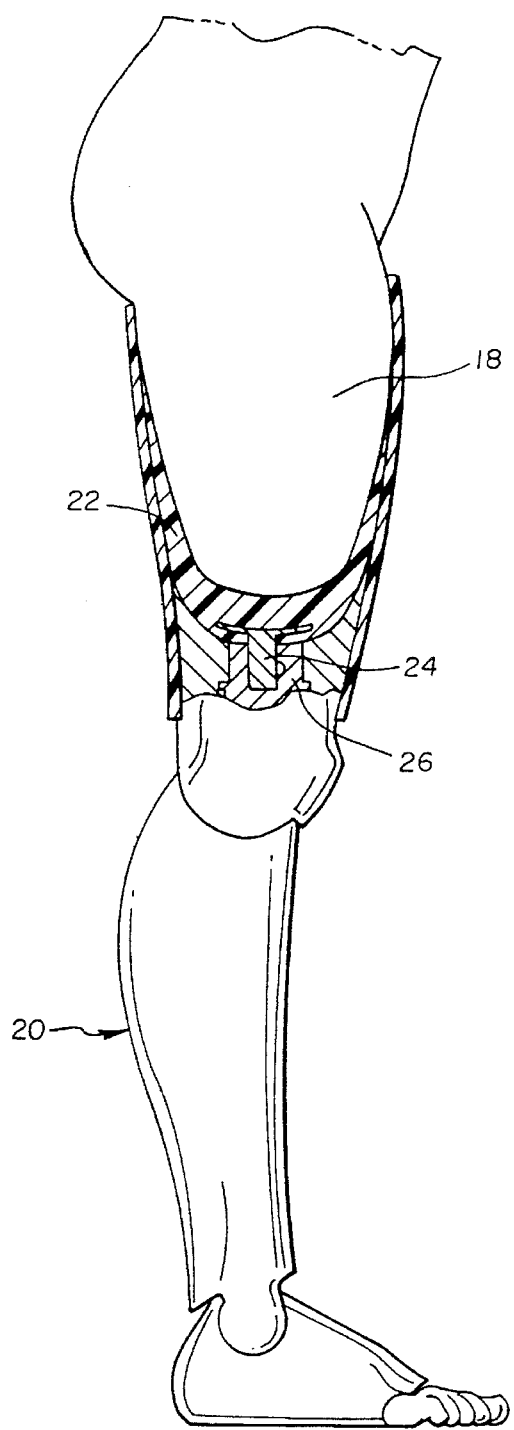
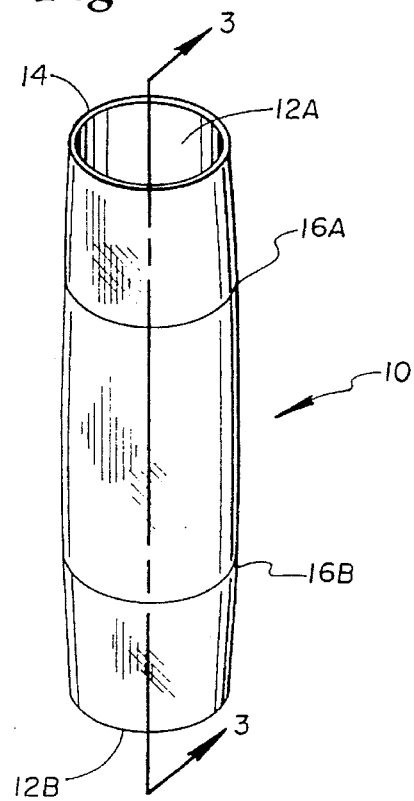
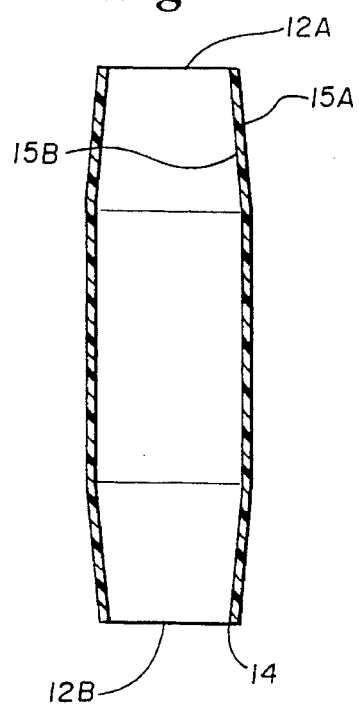

ARTIFICIAL LIMB MOUNTING APPARATUS

BACKGROUND OF THE INVENTION

1. Field of the Invention

The present invention relates to a soft elastomeric composite sleeve for use in attaching an artificial limb to the stump of an amputee. More specifically, the invention discloses a flexible barrel shaped polymeric elastomer support sleeve with integral mesh reinforcement which provides controlled stretch limits as well as soft and friendly gripping surface.

2. Description of the Prior Art

Elastic supports for attaching a prothesis are well known in the art. As examples, David Beldzinsky, in U.S. Pat. No. 4,479,272, discloses a plurality of sheaths which extend along a sleeve of a socket prosthesis. The outermost sheath is open at top and bottom and extends from above the sleeve down over the prosthesis itself to capture the prosthesis. An inner sheath, when attaching the prosthesis to an amputee, is first folded over the top edge of the outer sheath, and then folded again together with the outer sheath to form a welt abutting the upper edge of the prosthesis.

Michael R. Ross, in U.S. Pat. No. 4,908,037, discloses a sleeve for attaching a prosthesis to a partially amputated limb of the body of a patient. The sleeve is made of an elastomeric material which may have a tubular shape. Annular ribbing is formed on the inside wall of the sleeve at one end. The ribbing engages the limb and creates a suction-type seal to effect suspension of the prosthesis.

Jolly et al., in U.S. Pat. No. 4,822,371, disclose a reinforced elastic sleeve for use with a limb prosthetic device. This comprises an elastic suspension sleeve having two circular ends which enclose and grip the residual lower extremity of the patient and the prosthesis. The sleeve has an internal cylindrical-like panel which has a fabric surface with a low coefficient of friction. The internal panel serves to decrease irritation to the wearer and enhance longevity and strength of the sleeve.

None of these apparatus provide mesh reinforcement of an attachment sleeve or controlled stretch limits which are different along the length and circumference of the sleeve. Further, none provide a match between the enclosed flesh and the sleeve to reduce pressure points.

SUMMARY OF THE INVENTION

The present invention relates to an elastic suspension sleeve sized to fit over an amputee stump and a prosthesis. The sleeve is generally barrel shaped with open ends, and is formed into an open barrel shaped tube from polyurethane elastomer material or other soft elastomers having the characteristics later described. A barrel shape reduces the size of the sleeve ends and increases the gripping force for a given sleeve size. The design nature of the material will provide this firm gripping with soft, smooth and friendly contact with the skin and skin tissues.

The soft elastomeric material selected preferably has the resilience, impact absorption, load bearing capability and energy bearing of the patient's skin and underlying fat adjacent to the sleeve to reduce pressure point problems. The soft elastomeric material selected is also preferably tacky to facilitate positional maintenance and transparent so any possible remaining pressure point problems can be directly observed. The soft elastomeric material selected should also be able to elongate between 700% to 1,600% relative to the original dimension but subsequently recover to within one to five percent of the original unstretched dimensions. Thus, the elastomeric material should be very soft, stretchy, with a very high degree of elastic memory.

A reinforcing web, molded integral with the sleeve of nylon or polyurethane or material having similar strength and flexibility, controls the stretch parameters and allows the sleeve to stretch four times more around its circumference than along its length. This combination results in a sleeve which, because of the restriction in length stretch from the web reinforcement, grips the thigh and prosthesis firmly, but provides great attachment strength because of the longitudinal stretch restriction and web reinforcement. The additional stretch allowed around the circumference reduces the difficulty of stretching the sleeve over the stump and prosthesis. The web reinforcement also eliminates the problem of a failure where even a small puncture can cause cut propagation and complete loss of the sleeve, thus complete support loss. The fact that the material physical characteristics closely conform to that of the flesh of the patient underlying the sleeve, greatly reduces pressure points with their attendant problems. This composite of highly stretchable elastomer, with high memory, when arrested with the web encapsulation, provides a medium with controlled stretch and quick recovery as the amputee walks, bends, etc.

The sleeve's barrel shape greatly also reduces the problem of roll back along the edges present with previous approaches. This roll back is not only uncomfortable to the user, but also reduces the amount of contact surface which can result in a sleeve release. Further, the more the roll back, the sleeve will create pressure points on the skin as well as redness. Sleeve length thus reduces overall gripping.

DESCRIPTION OF THE DRAWINGS

FIG. 1 is a side elevational diagram in section showing the invention in use;

FIG. 2 is a perspective view of the sleeve alone;

FIG. 3 is a section taken generally along line 3—3 in FIG. 2;

DETAILED DESCRIPTION OF THE PREFERRED EMBODIMENTS

Sleeve 10, shown in FIGS. 2 and 3, is typically made of elastic polyurethane and is formed into a generally cylindrical shaped sheet having end openings 12A and 12B. Wall 14 of sleeve 10 has breaks 16A and 16B spaced inward from each respective end with an inward taper from the break to the sleeve end. This results in an essentially barrel shape for sleeve 10. This barrel shape provides smaller openings 12A and 12B at the ends of sleeve 10 than would a cylinder in order to provide a greater gripping tension for a given sleeve size. This barrel shape also resists roll over at the ends which otherwise causes attendant discomfort for the user.

A web, not shown in these figures, which conforms to the shape of sleeve 10, as depicted, is enclosed within wall 10 with the plane of the web lying between the outer surface 15A and the inner surface 15B of wall 14.

Figure 1A:
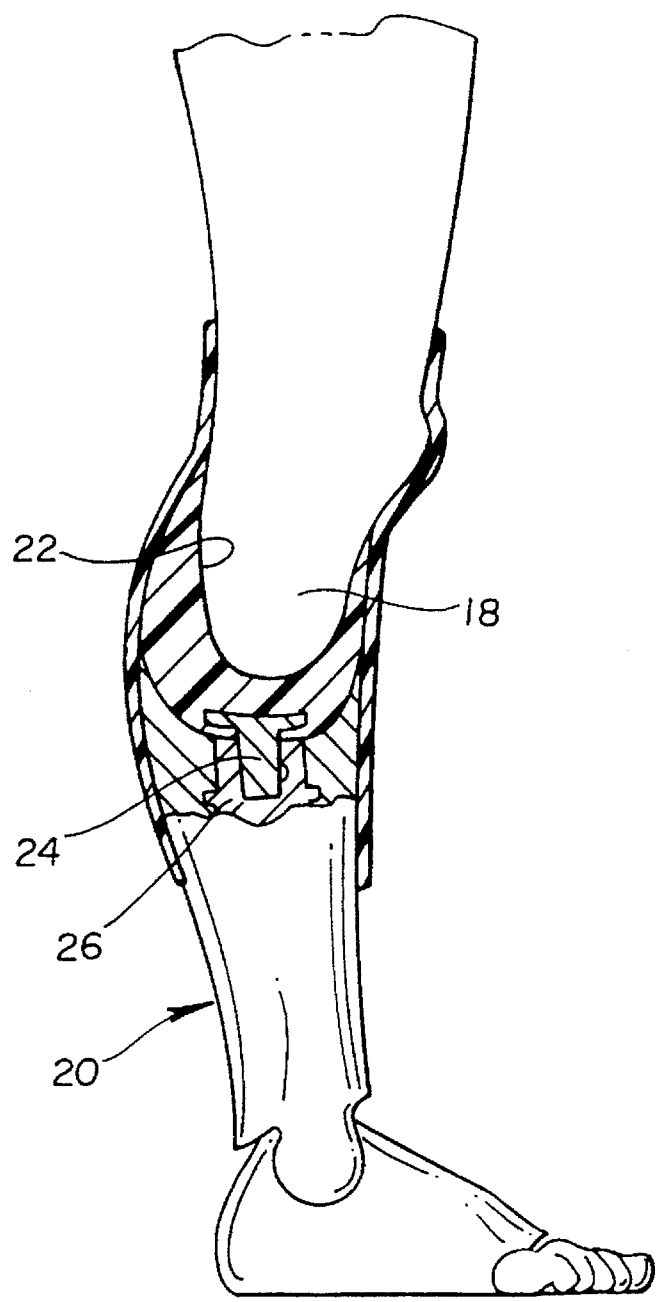
FIG. 1a is a view, similar to that of FIG. 1, showing the invention in use, as applied to an amputee, wherein the stump is below the knee.

In a typical prothesis attachment arrangement, shown here in FIG. 1 and FIG. 1a for illustration, the proximal end of prosthesis 20 has a receptacle 26 shaped to mate with a connector 24 extending downward from, and attached to, the distal end of liner 22 which covers a patient's stump 18. Typically, the stump is below the knee, as shown in FIG. 1a. While a number of other arrangements can be provided they all provide the stump with some sort of covering which attaches to, and mates with, a prosthesis. All of these require some sort of attachment means to securely attach a prosthesis to the stump.

Sleeve 10 is shown capturing a patient's stump 18 and the proximal end of a prosthesis 20. Liner 22 has a distal end which mates with the proximal end of prosthesis 20. Sleeve 10 must be stretched to effect engagement of liner 22 enclosing thigh 18 and the proximal end of prosthesis 20. This stretching provides the attachment means and attachment strength for maintaining the prosthesis to the stump.

The soft elastomeric composite material for sleeve 10 preferably closely resembles the resilience, impact absorption, load bearing capability and energy bearing capacity of the patient's skin and underlying fat tissue adjacent to the sleeve to reduce pressure point problems. The material used should preferably be transparent to permit direct observation of the stump and elimination of any such pressure point problems.

For optimum strength and ease of use, the soft elastomeric material selected for sleeve 10 must also be able to be elongated up to 700% to 1,600% of the original dimension but subsequently recover to within one to five percent of the original unstretched dimensions. The reasons for these requirements will be discussed hereinafter.

A reinforcing mesh 28, molded integral with sleeve 10 and lying between outer surface 15A and inner surface 15B within wall 14, is shown in FIGS. 4 through 9. Mesh 28 can be made of nylon strands, polyurethane, or similar material having similar strength and flexibility.

The strands of mesh 28 are arranged into two different weave patterns to provide two separate embodiments for controlling the stretch parameters and allow the sleeve to stretch approximately four times more around the circumference than along the length.

Figure 4:
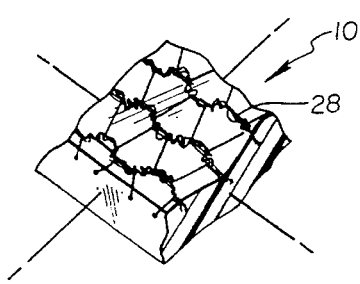
FIG. 4 is a fragmentary perspective detail, greatly enlarged, of mesh embedded within the sleeve wall.
Figure 5:
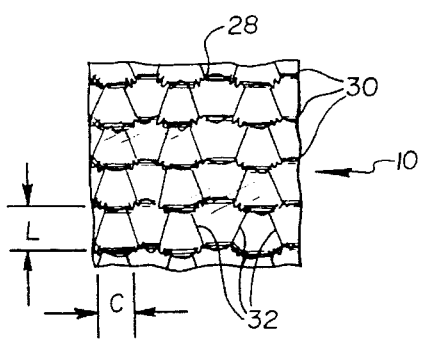
FIG. 5 is a simplified diagram of the mesh pattern relaxed.
Figure 6:
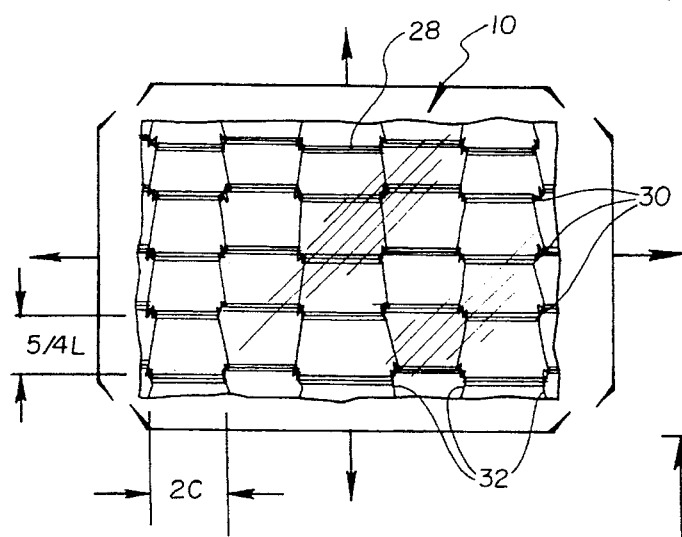
FIG. 6 is a simplified diagram of the mesh pattern in a stretched configuration.

FIGS. 4 through 6 show a first weave pattern where generally parallel strands 30 are intertwined with strands 32 to form a generally trapezoidal shaped pattern. A plurality of trapezoidal patterns are formed by generally parallel strands 30 intertwined with non-horizontal strands 32 which are arranged to form the sides of a repeating trapezoidal pattern. As shown in FIG. 5, strands 30 and 32 are oriented within sleeve 10 such that strands 30 lie generally along the circumference of the sleeve, while strands 32 lie generally along the length of the sleeve.

FIG. 6 shows sleeve 10 stretched along both directions with a resulting more rectangular shaped strand pattern. This naturally occurring resultant rectangular shape of a stretched trapezoidal pattern results in the circumference of sleeve 10 lying along strands 30 extending further than the length lying along strands 32, where the distance between strands 32 is extended apart approximately a factor of 2, and the distance between strands 30 is extended apart approximately a factor of 5/4. This results in a stretch limit along the length between strands 30 being one fourth the stretch limit around the circumference between strands 32.

Figure 7:
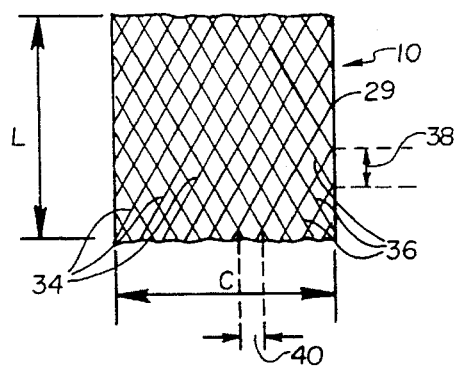
FIG. 7 is a simplified diagram of a diamond pattern in a relaxed configuration.
Figure 8:
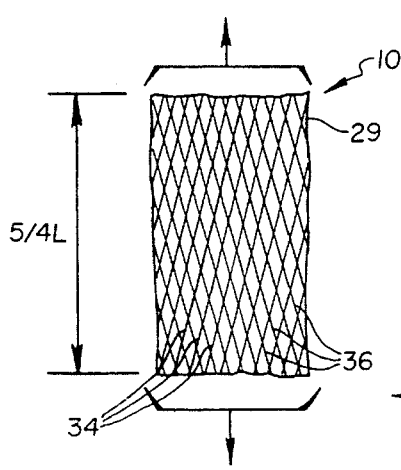
FIG. 8 is a simplified diagram of a diamond pattern stretched longitudinally.
Figure 9:
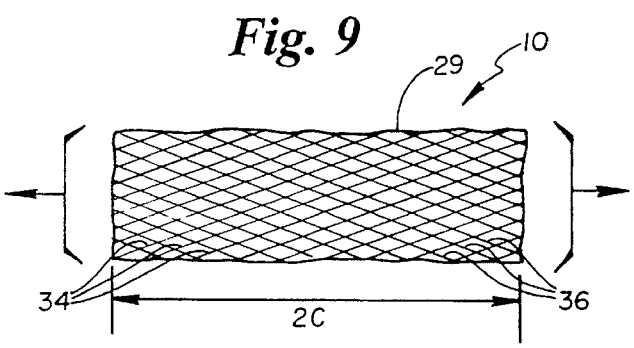
FIG. 9 is a simplified diagram of a diamond pattern stretched circumferentially.

FIGS. 7 through 9 show mesh 29 of nylon elastomer strands formed into a diamond shaped weave pattern where essentially parallel strands 34 are interwoven with essentially parallel strands 36, resulting in a plurality of diamond patterns, each with a longitudinal dimension 38 and a circumferential dimension 40. Longitudinal dimension 38 is made greater relative to circumferential dimension 40 by a ratio of 5/4 to 2.

As shown in FIG. 8, when sleeve 10 is stretched longitudinally, since the circumferential dimension is less then the longitudinal dimension the pattern will be elongated toward a near line after a relatively small amount of stretching. Conversely, as shown in FIG. 9, when sleeve 10 is stretched circumferentially the pattern will be elongated toward a near line after a relatively greater amount of stretching. Since sleeve 10 can only be stretched by extending strands 34 or 36 after the diamond pattern is collapsed into a straight line, the collapse of this pattern effectively limits the amount of stretching possible. Since the circumferential and longitudinal dimensions are unequal in length, the limit on the amount of stretch is different in these two directions. Making the ratio of the longitudinal dimension and circumferential dimension as specified above results in a circumference stretch which is limited to approximately twice the unstretched amount and a longitudinal stretch which is limited to approximately 5/4 the unstretched amount.

These two embodiments, both of which result in a smaller stretch limit along the length of sleeve 10 by a factor of one fourth relative to the stretch limit around the circumference, provide a number of advantages. The greater stretch limit around the circumference of sleeve 10 reduces the required force, and consequently the resulting difficulty, in attaching the ends of the sleeve to a stump 18 or a prosthesis 20, as well as forms a seal-like grip around the stump while maintaining soft and friendly contact.

The length stretch limit of sleeve 10 permits using polyurethane elastomeric material for the sleeve proper which is quite soft and closely matches the physical characteristics of the flesh enclosed. This greatly reduces any pressure point problems. If this stretch limit and web reinforcement were not provided, sleeve 10 would not optimally connect prosthesis 20 to stump 18 with optimal strength and gripping for practical use.

The use of a mesh 28 of nylon, polyurethane, or other material having similar strength and design, also inhibits another more serious failure problem which might result when a small cut, puncture or tear progresses completely across sleeve 10 and results in total support failure.

The two patterns disclosed here provide the desired stretch limit. However, a number of similar patterns which, when combined with the soft elastomeric sleeve of suitable material, may result in identical or similar stretch limits.

It will be understood that the ratio of stretch in the circumferential dimension to that in the longitudinal dimension can be different than that specifically identified hereinbefore (that is, 4:1). For example, a range of appropriate ratios might vary between 2:1 to 6:1. What is important is that the appropriate characteristics and features discussed herein be achieved.

The materials suggested here have the necessary physical characteristics and these suggestions are not intended to be limiting. Any materials which meet the material requirements described above can be substituted with identical or similar results.

While this invention has been described with respect to specific embodiments, these descriptions are not intended to be construed in a limiting sense. Various modifications of the illustrative embodiments, as well as other embodiments of the invention, will be apparent to persons skilled in the art upon reference to these descriptions. It is therefore contemplated that the appended claims will cover any such modifications or embodiments as fall within the true scope of the invention.

What is claimed is:

1. Apparatus for retaining a prosthesis securely to a stump of an amputee, comprising:

a) a single, enduringly resilient elastomeric sleeve having a generally open cylinder shape with opposed open first and second ends sized to secure a prosthesis to a stump, and having opposed outer and inner surfaces essentially parallel to one other; said sleeve having the property of being able to be stretched up to two times an original unstretched dimension without tearing, but when released return to substantially the original dimension; and b) said sleeve having a mesh reinforcement formed integral therewith and embedded therein; said mesh having perpendicular first circumferential and second longitudinal directions in a plane of said mesh; said mesh having stretch control means for controlling the total amount of sleeve stretch in different directions such that the total amount of stretch along the first direction is approximately in a range of two to six times the total amount of stretch along the second direction.

2. Apparatus as in claim 1 wherein said stretch control means comprises a mesh having a plurality of first and second intersecting and intertwined strands forming a plurality of generally trapezoidal shaped figures, with adjacent first strands forming parallel sides, and adjacent second strands forming nonparallel sides of the trapezoidal shaped figure, said first strands being oriented generally circumferentially with respect to said sleeve.

3. Apparatus as in claim 1 wherein said stretch control means comprises said mesh having a plurality of generally parallel first and generally parallel second strands, said first and second strands being intersecting and intertwined to form a plurality of generally diamond shape figures, said diamond shape having a long dimension and a short dimension, with the short dimension being aligned with the circumference of said sleeve.

4. Apparatus as in claim 1 wherein a diameter of said first and said second ends each diminish generally linearly from a predetermined distance from each respective end to said respective end.

5. Apparatus as in claim 1 wherein said sleeve is formed of elastomeric material having a resiliency, impact absorption, and energy absorption characteristics approximating that of the skin and fatty tissue properties of an enclosed stump adjacent to said sleeve.

6. Apparatus as in claim 1 wherein said sleeve is formed of transparent elastomeric material.

7. Apparatus as in claim 1, wherein said inner surface of said sleeve is tacky.

* * * * *

UNITED STATES PATENT AND TRADEMARK OFFICE
CERTIFICATE OF CORRECTION

PATENT NO. : 5,593,454
DATED      : January 14, 1997
INVENTOR(S): Nashat N. Helmy It is certified that error appears in the above-indentified patent and that said Letters Patent is hereby corrected as shown below:

Column 6, line 2 thereof, delete "a", first occurrence, and insert therefor --said--.

Signed and Sealed this

Eighth Day of April, 1997

Attest:

BRUCE LEHMAN

Attesting Officer

Commissioner of Patents and Trademarks